(12) United States Patent
Park et al.

(10) Patent No.: US 7,803,796 B2
(45) Date of Patent: Sep. 28, 2010

(54) HOMOPIPERAZINE COMPOUNDS THAT INHIBIT RIBOSOMAL FRAMESHIFTING BY BINDING TO RNA PSEUDOKNOT STRUCTURE OF SARS CORONAVIRUS

(75) Inventors: Hyun-Ju Park, Seoul (KR); So-Jung Park, Gyeonggi-do (KR); Yang-Gyun Kim, Seoul (KR)

(73) Assignee: Sungkyunkwan University Foundation For Corporate Collaboration, Gyeonggi-Do (KR)

( * ) Notice: Subject to any disclaimer, the term of this patent is extended or adjusted under 35 U.S.C. 154(b) by 0 days.

(21) Appl. No.: 11/961,781

(22) Filed: Dec. 20, 2007

(65) Prior Publication Data

US 2008/0207597 A1    Aug. 28, 2008

(30) Foreign Application Priority Data

Dec. 22, 2006    (KR) .................... 10-2006-0132761

(51) Int. Cl.
*A61K 31/426* (2006.01)
*A61K 31/381* (2006.01)
*A61K 31/215* (2006.01)

(52) U.S. Cl. .................... 514/218; 514/365; 514/439; 514/506

(58) Field of Classification Search .................... None
See application file for complete search history.

(56) References Cited

FOREIGN PATENT DOCUMENTS

| JP | 2000-119253 | 4/2000 |
|---|---|---|
| JP | 2000-143623 | 5/2000 |
| JP | 2001-261657 | 9/2001 |
| JP | 2007-016041 | 1/2007 |

OTHER PUBLICATIONS

Dorwald, F.A., Side Reactions in Organic Synthesis, 2005, Wiley: VCH, Weinheim, pg. IX.*

* cited by examiner

*Primary Examiner*—James D Anderson
*Assistant Examiner*—Gregg Polansky
(74) *Attorney, Agent, or Firm*—Rabin & Berdo, P.C.

(57) ABSTRACT

Provided is a homopiperazine compound for inhibiting ribosomal frameshifting by binding to an RNA pseudoknot structure of SARS coronavirus. Particularly, the present invention provides a pharmaceutical composition for inhibiting synthesis of protein induced by −1 frameshifting by binding to an RNA pseudoknot structure specifically existing in SARS coronavirus. The composition includes a therapeutically effective amount of homopiperazine compound of following chemical formula 1 or a pharmaceutically accepted salt thereof, and a pharmaceutically accepted carrier or excipient.

8 Claims, 5 Drawing Sheets

HOMOPIPERAZINE COMPOUNDS THAT INHIBIT RIBOSOMAL FRAMESHIFTING BY BINDING TO RNA PSEUDOKNOT STRUCTURE OF SARS CORONAVIRUS

CROSS-REFERENCE(S) TO RELATED APPLICATIONS

The present invention claims priority of Korean Patent Application No. 10-2006-0132761, filed on Dec. 22, 2006, which is incorporated herein by reference.

BACKGROUND OF THE INVENTION

1. Field of the Invention

The present invention relates to a compound useful for antiviral treatment and prevention of virus-induced diseases, and a pharmaceutical composition including the same.

2. Description of Related Art

Severe Acute Respiratory Syndrome (SARS) has broken out in an area around Canton, China in November, 2002 and spread all around the world. The syndrome features such symptoms as fever, difficulty in breathing, atypical pneumonia and the like. The cures for the syndrome have not been revealed sufficiently. Some practitioners treat patients with antibiotics or antiviral drugs but the effect is not satisfactory and the death rate keeps on increasing. This calls for immediate development of effective cures for SARS. The present invention is based on this pressing need.

Most antiviral drugs developed to treat virus-induced diseases target on protein that is essential for viability of the virus. Such drugs seem effective at first but virus acquires resistance to the drugs soon in the course of treatment period. This is because virus protein mutates rapidly, and the drugs targeting the protein do not work for the virus any more.

Therefore, it is important to prevent virus from acquiring resistance to drugs. One of the solutions to this problem is to develop a drug targeting a specific structure of ribonucleic acid (RNA) in viruses instead of targeting protein, because resistance to site-specific mutagenesis emerges relatively slowly. However, there is few compound developed as an antiviral drug targeting RNA structure. An RNA pseudoknot structure is a novel target, which is an essential factor for −1 ribosomal frameshifting, an important mechanism of protein synthesis in SARS coronavirus.

SUMMARY OF THE INVENTION

An embodiment of the present invention devised to overcome the limitation of conventional antiviral drugs by targeting an RNA pseudoknot structure of SARS coronavirus is directed to providing an antiviral compound which has excellent activity in inhibiting viability of the SARS coronavirus and minimizes resistance to cure drugs to be useful as an antiviral drug, and a pharmaceutical composition including the antiviral compound.

Other objects and advantages of the present invention can be understood by the following description, and become apparent with reference to the embodiments of the present invention. Also, it is obvious to those skilled in the art to which the present invention pertains that the objects and advantages of the present invention can be realized by the means as claimed and combinations thereof.

In accordance with an aspect of the present invention, there is provided a pharmaceutical composition for inhibiting synthesis of protein induced by −1 frameshifting by binding to an RNA pseudoknot structure specifically existing in SARS coronavirus, which includes: a therapeutically effective amount of homopiperazine compound of chemical formula 1 or a pharmaceutically accepted salt thereof, and a pharmaceutically accepted carrier or excipient.

In accordance with another aspect of the present invention, there is provided a pharmaceutical composition for antiviral treatment or prevention of virus-induced diseases, which includes: a therapeutically effective amount of homopiperazine compound of chemical formula 1 or a pharmaceutically accepted salt thereof, and a pharmaceutically accepted carrier or excipient.

DESCRIPTION OF SPECIFIC EMBODIMENTS

Figure 1:
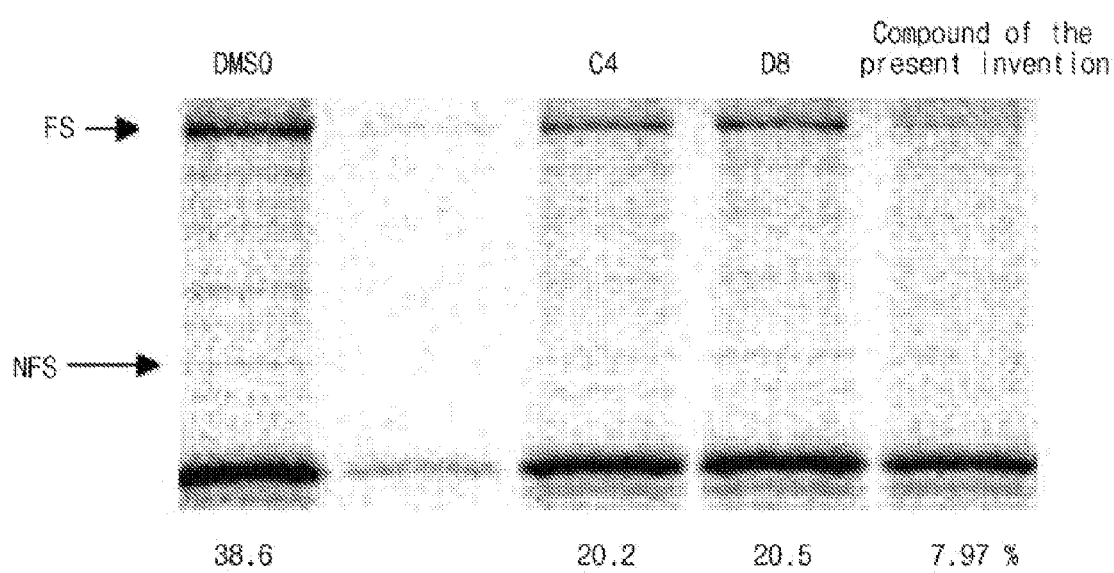
FIG. 1 shows −1 frameshifting efficiencies induced by RNA pseudoknot of SARS coronavirus in the presence of tested compounds determined by sodium dodecyl sulfate polyacrylamide gel electrophoresis (SDS-PAGE).

The advantages, features and aspects of the invention will become apparent from the following description of the embodiments with reference to the accompanying drawings, which is set forth hereinafter.

−1 frameshifting is one of mechanisms for synthesizing different proteins with one messenger RNA (mRNA). The −1 frameshifting produces two different proteins by using a translation frame shifted by −1, that is, by using a frame shifted from a normal translation frame as much as one frame in 5' direction, at a specific site. SARS coronavirus produces more than two kinds of proteins needed for self-replication at an exact ratio by using the −1 frameshifting caused by the RNA pseudoknot structure in host cells. An increase or decrease in the efficiency of the −1 frameshifting may induce a fatal result such as suppressed or destroyed self-replication process of the coronavirus.

The RNA pseudoknot structure is known to play a significant role in the efficiency of the −1 frameshifting. To be specific, the structural features and stability of RNA pseudoknot are important in maintaining the exact efficiency of the −1 frameshifting. The inventors of the present invention selected candidate compounds by virtual screening of commercially-available chemical database containing hundreds and thousands of compounds targeting the three-dimensional RNA pseudoknot structure model of the SARS coronavirus, and assayed −1 frameshifting efficiency through in-vitro and cell-based experiments. This way, they developed a compound of the following chemical formula 1, which is a low-molecular weight compound that may suppress the synthesis of protein essential for the viability of the SARS coronavirus from the initial synthesis step through target selection and method differentiated from conventional new medicine development.

[Chemical Formula 1]

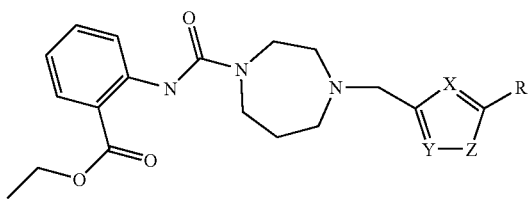

where R denotes H, alkyl including 1 to 6 carbon atoms, aryl including 3 to 10 carbon atoms, or heteroaryl including N or O interposed between carbon atoms of aryl;

X and Y denote carbon or nitrogen independently; and

Z denotes oxygen, sulfur, or nitrogen.

The X, Y and Z may be substituted or unsubstituted by halogen, or alkyl having 1 to 6 carbon atoms.

The following Table 1 shows preferable compounds among the compounds of the chemical formula 1.

TABLE 1

| Sample No. | Chemical Formula of Compound | Name of Compound |
|---|---|---|
| 1 |  | 2-((4-(2methyl-thiazole-4-ylmethyl)-[1,4]diazepene-1-carbonyl)amino)benzoic acid ethyl ester |
| 2 |  | 2-((4-[5-(3,5-dimethyl-isoxazole-4-yl)-[1,2,4]oxadiazole-3-ylmethyl]-[1,4]diazepane-1-carbonyl)-amino)-benzoic acid ethyl ester |
| 3 |  | 2-((4-(5-methyl-isoxazole-3-ylmethyl)-[1,4]diazepane-1-carbonyl)-amino)-benzoic acid ethyl ester |

TABLE 1-continued

| Sample No. | Chemical Formula of Compound | Name of Compound |
|---|---|---|
| 4 | | 2-((4-(5-chloro-1,3-dimethyl-1H-pyrazol-4-ylmethyl)[1,4]diazepane-1-carbonyl)-amino)-benzoic acid ethyl ester |

The present invention includes not only the homopiperazine compounds expressed as the chemical formula 1 and their pharmaceutically acceptable salts but also solvates and hydrates that can be prepared with them.

The compounds of the chemical formula 1 can be used in the form of pharmaceutically acceptable salts, and acid-added salts formed of pharmaceutically acceptable free acids are useful. As for the free acids, organic acid and inorganic acid can be used. Examples of the inorganic acid include hydrochloric acid, phosphoric acid, sulphuric acid, and nitric acid. Examples of the organic acids include methanesulphonic acid, p-toluenesulphonic acid, acetic acid, trifluoroacetic acid, citric acid, maleic acid, succinic acid, oxalic acid, benzoic acid, tartaric acid, fumaric acid, manderic acid, propionic acid, lactic acid, glycollic acid, gluconic acid, galacturonic acid, glutamic acid, glutaric acid, glucuronic acid, aspartic acid, ascorbic acid, carbonic acid, vanillic acid, and iodic acid.

According to the present invention, the acid-added salts can be prepared through conventional methods. For example, acid-added salt can be prepared by dissolving a compound of the chemical formula 1 in an excessive amount of an acid aqueous solution, and precipitating the salt in a water-miscible organic solvent, such as methanol, ethanol, acetone or acetonitrile. Acid-added salt can be also prepared by heating a mixture including the same amount of the compound of the chemical formula 1 and an acid in water or alcohol such as glycol monomethylether, and then drying the mixture or performing suction filtration onto the educed salt.

It is also possible to prepare the acid-added salt by dissolving the compound of the chemical formula 1 in an organic solvent, for example, diethyl ether, tetrahydrofuran, dichloromethane, or acetonitrile, adding the aforementioned inorganic or organic acids thereto directly or in the form of being dissolved in the organic solvent to thereby form salt, precipitating the salt, and performing suction filtration onto the salt.

The compound of the chemical formula 1 can be formulated into diverse types of pharmaceutical preparations to be administered orally or parenterally in clinical studies. More specifically, it can be prepared by using the typical additives such as a filler, a diluent, a binder, a wetting agent, a disintegrating agent, a surfactant and an excipient.

Solid preparations for oral administration are tablets, pills, powder, granules, capsules and so forth. These solid preparations are manufactured by adding at least one excipient such as starch, calcium carbonate, sucrose, lactose, or gelatin to one or more compounds of the chemical formula 1. In addition, lubricants such as magnesium stearate, and talc may be used in addition to the typical excipients.

Liquid preparations for oral administration are suspensions, oral liquid, emulsions, syrups, and various excipients such as a wetting agent, a sweetener, an aromatic agent, a preservative may be used in addition to typical diluents such as water and liquid paraffin.

Preparations for parenteral administration are a sterile water-soluble liquid, a water-insoluble solvent, suspensions, emulsions, a lyophilized drug and suppositories. Examples of water-insoluble solvents and suspensions are vegetable oils such as propylene glycol, polyethylene glycol, and olive oil, and injectable esters such as ethylolate. Examples of the base for suppositories are witepsol, marcrogol, Tween 61, cacao butter, Sedum Laurinumn, glycerol, gelatin and the like.

The content of active ingredients of the preparations in the present invention can be adjusted appropriately according to the absorptivity, the rate of inactivation, rate of excretion of the active ingredients, age, sex and health conditions of a patient.

The compound of the chemical formula 1 is preferably administered in the range of about 0.1 to about 500 mg/kg/day for an adult, more preferably about 1 to about 20 mg/kg/day. The amount may be administered at once or several times daily.

Hereinafter, the present invention will be described in detail with reference to examples. The following examples only illustrate the present invention and the scope of the present invention is not limited to them.

EXAMPLE 1

In-Vitro −1 Frameshifting Assay of the Compound of the Present Invention

The compounds of samples 1 to 4 shown in the Table 1 were commercially acquired from Tripos Discovery Research Centre, Bude-Stratton Business Park, Bude, and Cornwall EX23 UK. The compound of the sample 1 was acquired from Leadgenex Inc. after ordering mass synthesis for the following cell-based assay.

Protein induced by −1 frameshifting was synthesized using a TNT T7-coupled transcription/translation system. Recombinant DNA plasmid containing a dual luminescence reporter gene with an RNA pseudoknot structure of SARS coronavirus inserted thereto was manufactured and used for tests. A solution was prepared to include 500 ng DNA, 10 μl rabbit reticulocyte lysate mixture, and methionine-labeled $^{35}$S 0.8 μl of a concentration of 10 μCi/μl. The final volume of the solution was 20 μl. Then, 2.5 mM compound (sample 1) dissolved in dimethyl sulfoxide (DMSO) was added to the mixture solution and placed at about 30° C. for about 2 hours. The amount of synthesized protein was assayed using SDS-PAGE and dual luciferase.

Result Analysis 1: SDS-PAGE

To separate non-frameshifting protein from −1 frameshifting protein, 12% stacking gel and 5% running gel were electrophoresed, exposed on a phosphoimager screen, and radiographed with BAS. The resulting acquisition was quantitated. The −1 frameshifting efficiency was calculated based on an equation of %=(I[FS]/26)/[(I[FS]/26)+I[NFS])/9]×100 in consideration of the number of $^{35}$S-methionines included in the proteins synthesized in the reaction. Herein, 1[FS] denotes the amount of the frameshifting protein, and I[NFS] denotes the amount of non-frameshifting protein. The result of the aforementioned compound is shown in FIG. 1.

As a result of assaying the −1 frameshifting effect, it was found that the compound of the present invention remarkably inhibited synthesis of frameshifting protein, compared to other compounds. DMSO was a control sample without the compound of the present invention, and the others included the compound of the present invention (2.5 mM).

Result Analysis 2: Dual Luciferase Assay

Figure 2:
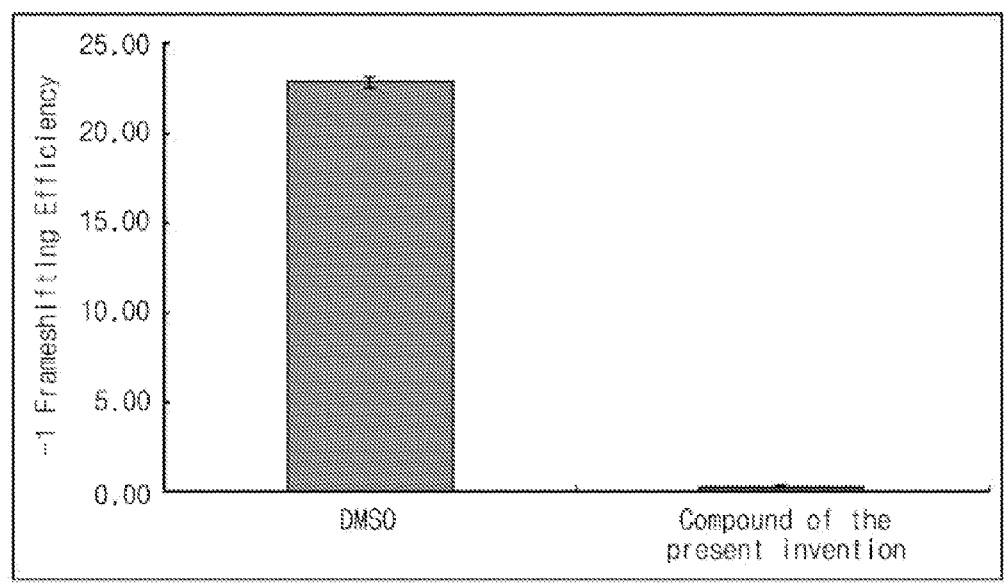
FIG. 2 is a graph sowing a −1 frameshifting efficiency measured by dual luciferase assay in the presence of a compound of the present invention.

Dual luciferase assay is a test for determining −1 frameshifting efficiencies by directly measuring the amount of synthesized reporter proteins as luciferase activities. A sample acquired from in-vitro transcription/translation coupled assay was taken about 1 μl and the amount of firefly luciferase was measured by adding about 50 μl of luciferease assay reagent II to the sample. Then, renilla luciferase was quantitated by adding about 50 μl of Stop & Glo reagent and using TD-20/20 luminometer. The result was presented in FIG. 2.

The result showed that the compound of the present invention remarkably inhibited synthesis of frameshifting protein. The DMSO was a control sample without the compound of the present invention, and the others included the compound of the present invention (2.5 mM).

EXAMPLE 2

Specificity Test of the Compound of the Present Invention for RNA Pseudoknot Structure of SARS Coronavirus The above-described method was applied to RNA pseudoknot structure of SARS coronavirus and another RNA pseudoknot structure without similarity thereto, and the results were comparatively analyzed. The −1 frameshifting effect of the compound of the present invention was as follows.

Result Analysis 1

Figure 3:
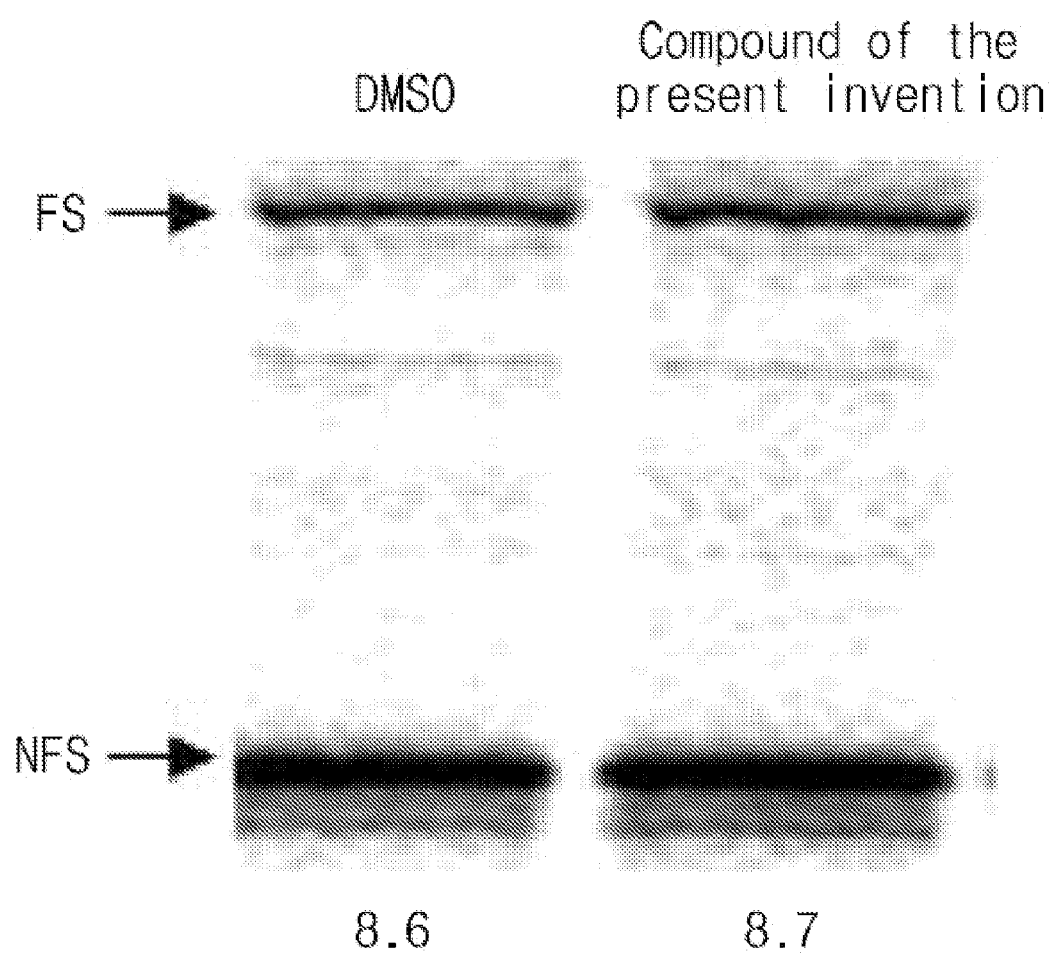
FIG. 3 shows −1 frameshifting assay results using the −1 ribosomal frameshifting system containing RNA pseudoknot of which structure is totally different from RNA pseudoknot structure of SARS coronavirus in the presence of the compound of the present invention.

The analysis results were shown in FIG. 3. The results showed that the compound of the present invention does not affect the other RNA pseudoknot structure that does not have similarity to the RNA pseudoknot structure.

Result Analysis 2

Figure 4:
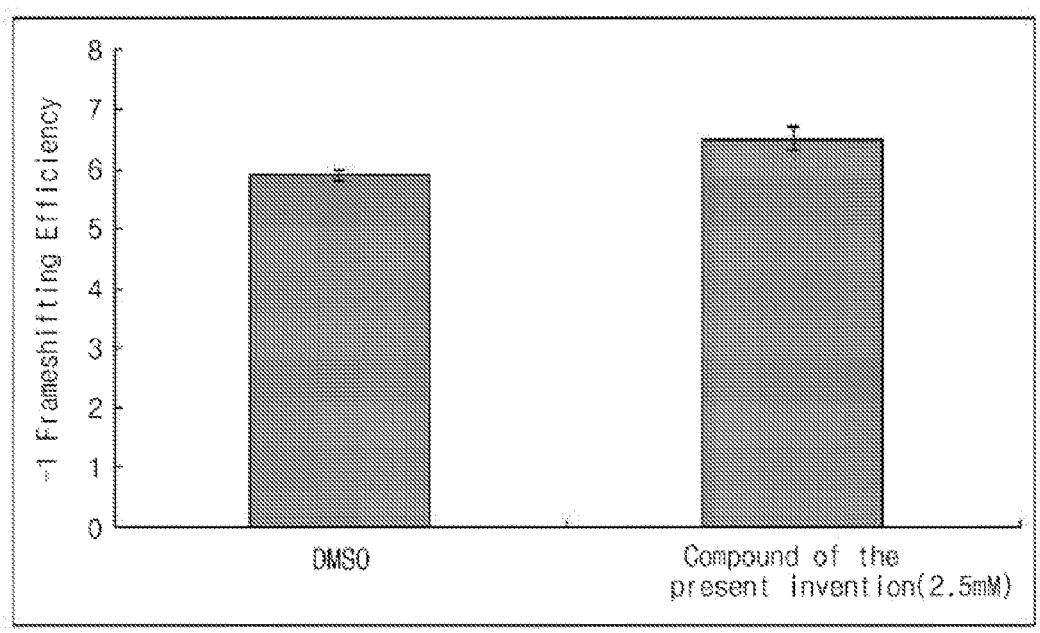
FIG. 4 is a graph representing a −1 frameshifting efficiency measured by dual luciferase assay for the same samples in FIG. 3

The analysis results were shown in FIG. 4. The results reconfirmed that the compound of the present invention does not affect the other RNA pseudoknot structure that does not have similarity to the RNA pseudoknot structure.

EXAMPLE 3

In-vitro −1 Frameshifting Assay

HEK 293 (Human Kidney cell) was used in experiments. For cell culturing, DMEM solution supplemented with 10% fetal bovine serum (FBS), penicillin and streptomycin and was used as a culture medium. The cells were cultured at 37° C. under the condition of 5% carbon dioxide and 95% atmosphere, and they were subcultured once every 3 to 4 days.

EXAMPLE 4

In-vitro −1 Frameshifting Assay of the Compound of the Present Invention

Cells were divided into a 24-well plate. The 24-well plate was cultured for 24 hours so that the cell fractions adhered to the bottom of the plate. After the cells adhered to the bottom, DNA including RNA pseudoknot structure of SARS coronavirus was injected to the wells and incubated for about 18 hours. Then, the compound (sample 1) of the present invention was added to the wells, 2 μl per well, and the well plates was incubated for another 18 hours. After the incubation was completed, the effect of the compound of the present invention on the −1 frameshifting was assayed using the dual luciferase method.

Figure 5:
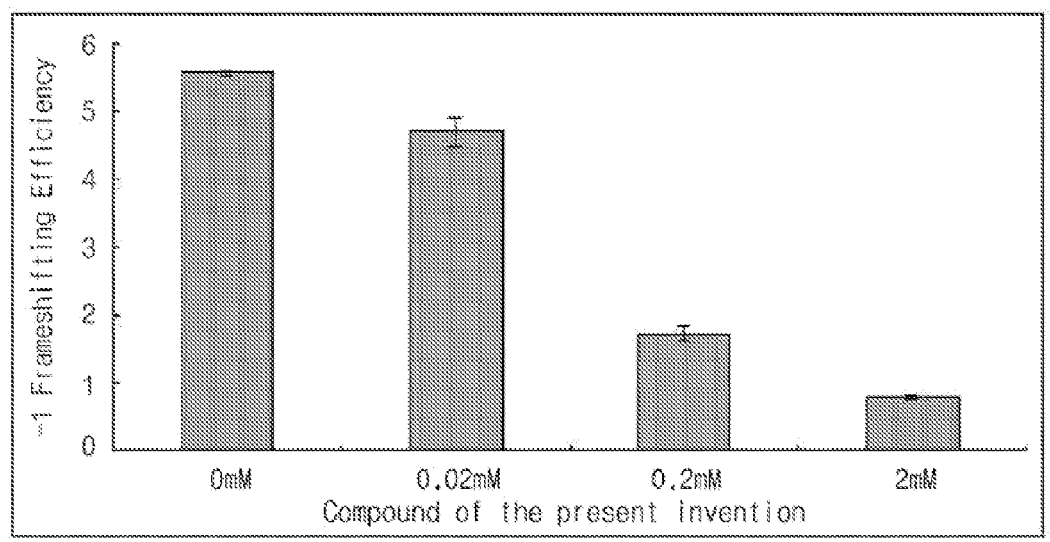
FIG. 5 is a graph showing a −1 frameshifting efficiency of the compound of the present invention measured by cell-based experiments.

The assay result was shown in FIG. 5. The assay result showed that the compound of the present invention inhibited synthesis of frameshifting protein. In the drawing, 0 mM is a control sample without the compound of the present invention, and the others included the compound (0.02 to 2 mM) of the present invention.

As describe above, the compound of the present invention binds to the RNA pseudoknot structure specifically existing in SARS coronavirus, which is a causal virus of SARS and inhibit synthesis of protein induced by −1 frameshifting to thereby work as an antiviral drug.

While the present invention has been described with respect to the specific embodiments, it will be apparent to those skilled in the art that various changes and modifications may be made without departing from the spirit and scope of the invention as defined in the following claims.

What is claimed is:

1. A pharmaceutical composition for inhibiting synthesis of protein induced by -1 frameshifting by binding to an RNA pseudoknot structure specifically existing in SARS coronavirus, comprising: a therapeutically effective amount of a homopiperazine compound of the following chemical formula 2 or a pharmaceutically accepted salt thereof, and a pharmaceutically accepted carrier or excipient:

2. A pharmaceutical composition for antiviral treatment of virus-induced diseases, comprising: a therapeutically effective amount of homopiperazine compound of the following chemical formula 2 or a pharmaceutically accepted salt thereof, and a pharmaceutically accepted carrier or excipient

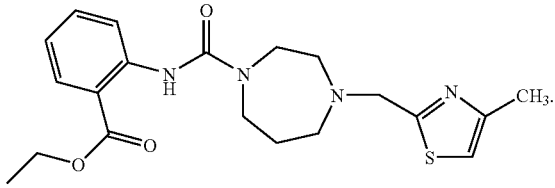

2

3. The pharmaceutical composition of claim 2, wherein the virus is SARS coronavirus.

4. The pharmaceutical composition of claim 2, which has a dosage form for oral administration.

5. The pharmaceutical composition of claim 2, which has a dosage form for parenteral administration.

6. The pharmaceutical composition of claim 1, which has a dosage form for oral administration.

7. The pharmaceutical composition of claim 1, which has a dosage form for parenteral administration.

8. A compound having the following name:
2-((4-(2-methyl-thiazole-4-ylmethyl)-[1,4]diazepene-1-carbonyl)amino)benzoic acid ethyl ester.

* * * * *